United States Patent [19]

Tuseth

[11] 4,078,563

[45] Mar. 14, 1978

[54] DISC VALVE IN A CONTAINER FOR DISPENSING LIQUIDS

[75] Inventor: Robert D. Tuseth, Union City, Calif.

[73] Assignee: Cutter Laboratories, Inc., Berkeley, Calif.

[21] Appl. No.: 694,873

[22] Filed: Jun. 10, 1976

[51] Int. Cl.² .............................................. A61M 5/16
[52] U.S. Cl. ................................ 128/214 C; 128/227; 137/192; 137/399; 137/433; 222/67
[58] Field of Search ............ 128/214 R, 214 C, 214.2, 128/227; 222/67; 137/433, 399, 192

[56] References Cited

U.S. PATENT DOCUMENTS

| | | | |
|---|---|---|---|
| 1,857,409 | 5/1932 | Smith | 137/433 X |
| 2,074,223 | 3/1937 | Horiuchi | 128/214 B |
| 2,513,862 | 7/1950 | Hart | 137/433 X |
| 3,191,608 | 6/1965 | Licata | 137/433 X |
| 3,216,419 | 11/1965 | Scislowicz | 128/214 C |
| 3,965,895 | 6/1976 | Dabney | 128/214 C |

Primary Examiner—Dalton L. Truluck
Attorney, Agent, or Firm—Robert E. Allen; Bertram Bradley

[57] ABSTRACT

An improved disc valve in a container for dispensing liquids is disclosed. The disc valve comprises at least two upstanding posts adjacent an outlet passage in the bottom of the container and a floatable disc member with apertures near its periphery through which the posts extend. The posts further have disc-retaining stops at their upper ends. The posts position the disc and the relationship between the size of the apertures and the thickness of the posts assures the disc will seat over the outlet passage to prevent the passage of air when all the liquid has been dispensed.

8 Claims, 7 Drawing Figures

DISC VALVE IN A CONTAINER FOR DISPENSING LIQUIDS

BACKGROUND OF THE INVENTION

This invention relates to an apparatus for dispensing a liquid and more particularly to an apparatus having improved means for automatically preventing the passage of air after a predetermined amount of the liquid has been dispensed.

There are a number of operations where it is desired to deliver a discrete volume of a liquid without an attendant having to be present to terminate the flow of the liquid at the right time. For example, in the administration of parenteral solutions, particularly to pediatric patients, it is often critical that only a relatively small predetermined volume of the solution be given. It is a common practice in such cases to fill a metering container as part of an administration set with a known volume of the solution.

To avoid the possibility of air from entering the bloodstream of the patient, such metering containers have some form of valve or closure means at the bottom of the container which are intended to close the outlet at the bottom of the container when the solution level reaches this point. Typical of such valved metering devices are those disclosed in U.S. Pat. No. 3,216,419 wherein the valve comprises either a freely floating disc designed to close off the outlet when the level of the solution reaches the outlet or a floating disc anchored over the outlet at the bottom of the metering container by a flexible hinge. Experience has shown that valves of these types can not always be depended upon to close the outlet passage. The freely floating disc will sometimes stick to the side of the container and in the hinged variety, the disc will occasionally cant from the horizontal so as to prevent the disc from sealing the outlet.

Some metering containers have the floating disc retained about the outlet by a cage such as the devices in U.S. Pat. Nos. 3,625,211 and 3,774,603. These disc valves also fail to provide assurance of closing off the outlet since the cage structure tends to trap air bubbles, particularly when a liquid such as blood is being administered, so that the disc will not seal.

In the use of metered containers, the administration of a second or additional prescribed volume of solution is often desired, following the delivery of the first volume. When the additional solution is added to the metered container, the disc adheres to the bottom of the container and must be dislodged before the solution can flow to the patient. This is generally accomplished by squeezing a deformable member located below the metering chamber, such as a flexible drip chamber, which forces air up from the deformable member to unseat the disc and allow it to float. This dislodging operation is often difficult to achieve, particularly when the disc covers too large an area.

A disc valve for a blood transfusion apparatus is disclosed in U.S. Pat. No. 2,074,223, in which a disc is slidingly retained over an outlet by two posts near the periphery of the disc. The valve is designed so that the disc lifts off the outlet when blood flows upwardly against the disc but closes to prevent back flow of blood. There are no details to indicate whether such a valve would function in a metering container of the type described above.

Objects of the present invention are, therefore, to provide an apparatus for dispensing liquid which includes a floating disc valve capable of assuring closure to prevent the passage of air following delivery of liquid from the apparatus and to provide a disc valve in which the disc is easily dislodged from a sealing position prior to delivery of liquid.

SUMMARY OF THE INVENTION

The dispensing apparatus of the present invention comprises a generally tubular container whose top wall includes an air passage and an inlet passage for entry of liquid into the container from a supply of liquid. The bottom wall of the container has an outlet passage and a floating disc valve operatively associated with the outlet passage. The disc valve comprises at least two posts spaced apart and extending generally vertically from the floor of the bottom wall adjacent the outlet passage with disc-retaining means at the upper end of the posts. A flexible disc adapted for floating on the liquid has at least two spaced apertures near its periphery through which the posts extend, the posts locating the disc so that an unapertured central portion of the disc will always be positioned over or engage the outlet passage. The width of the apertures in the disc through which the posts extend are at least about twice the thickness of the posts in order to assure that the disc does not hang up on the posts in the event the disc should become canted relative to the posts. This relationship between aperture size and post thickness provides optimum conditions whereby there is a minimum of contact between the curved surface of the disc at the edge of the aperture and the much smaller curved surface of the post even when the disc becomes canted.

A preferred embodiment of the disc valve has only two spaced posts but other embodiments in which there are three or more posts are also functional as long as the posts position the disc so as to maintain its unapertured portion over the outlet passage. The disc can have more peripheral apertures than the number necessary for the posts to extend through. It is sometimes advantageous to provide these additional apertures so that air, which may become trapped below the disc, can escape upwardly more easily through these apertures.

The invention will be better understood and additional objects and advantages will become more apparent from the description and claims which follow.

DESCRIPTION OF THE PREFERRED EMBODIMENTS

Figure 1:
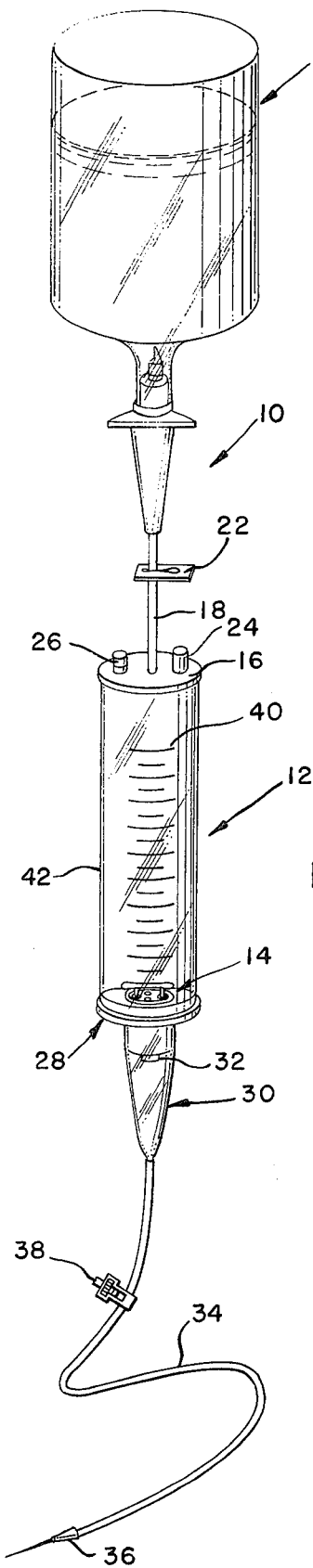
FIG. 1 is a perspective view of an embodiment of the invention in operative association with an administration apparatus.
Figure 2:
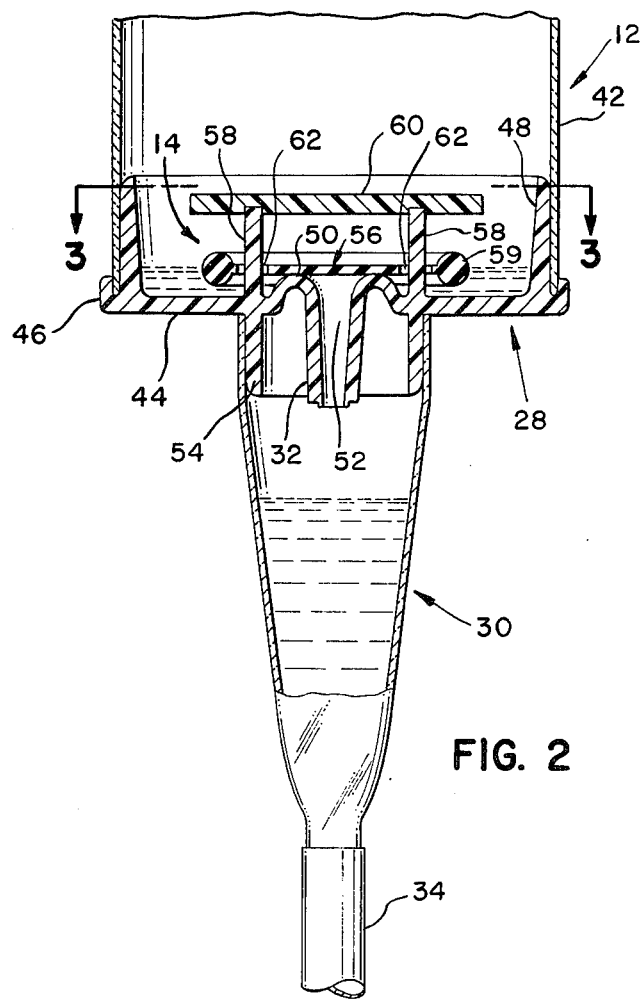
FIG. 2 is a fragmentary side elevational view, partially in vertical section, of a metering container of FIG. 1 with a drip chamber attached and showing a valve means in closed position.
Figure 3:
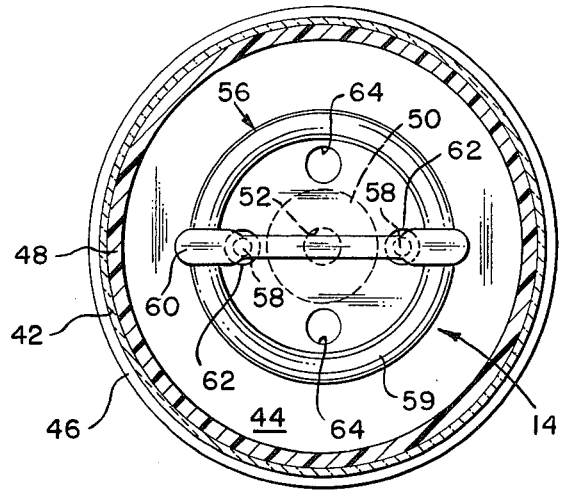
FIG. 3 is a top plan view taken along the line 3—3 of the valve means in FIG. 2.

FIG. 1 illustrates an administration apparatus 10 including a metering container 12 with an improved valve means 14 in accordance with the present invention. The metering container 12 has an inlet passage in its upper end wall 16 which is connected by conduit 18 leading to a solution container 20. Flow of liquid from container 20 is controlled by a clamp 22. The end wall 16 also has an airway 24 and may also have a medicinal entry port 26.

Metering container 12 has a lower end wall 28 to which is secured a deformable member or flexible drip chamber 30 surrounding an outlet or drip tube 32. The drip chamber 30 has its lower end connected by conduit 34 to an infusion needle 36 with an adjustable clamp 38 on conduit 34 to regulate the rate of flow of liquid from the metering container. Metering container 12 has suitable indicia 40 on its side wall 42.

Lower end wall 28 of metering container 12 has a flat bottom wall section 44 with two upstanding peripheral projections 46 and 48 spaced slightly apart between which is sealed the side wall 42 of the container. Spaced centrally on bottom 44 is a slightly upwardly projecting bead or annular valve seat 50 which converges into outlet passage 52 as defined by drip tube 32. A tubular projection 54 extending below the bottom wall 44 and spaced apart from drip tube 32 provides the means for sealing the drip chamber 30 to the metering container. Flexible drip chamber 30 need not be attached directly to the metering container 12. For example, drip tube 32 can be connected by tubing to a flexible drip chamber lower in the set. In fact, a conventional drip chamber can be replaced by a resiliently deformable member such as a small squeeze bulb as long as the bulb has a volume sufficient to displace a sealing disc seated over outlet passage 52. With a squeeze bulb arrangement, some form of liquid flow indicator associated with the conduit 34 should be included.

Figure 4:
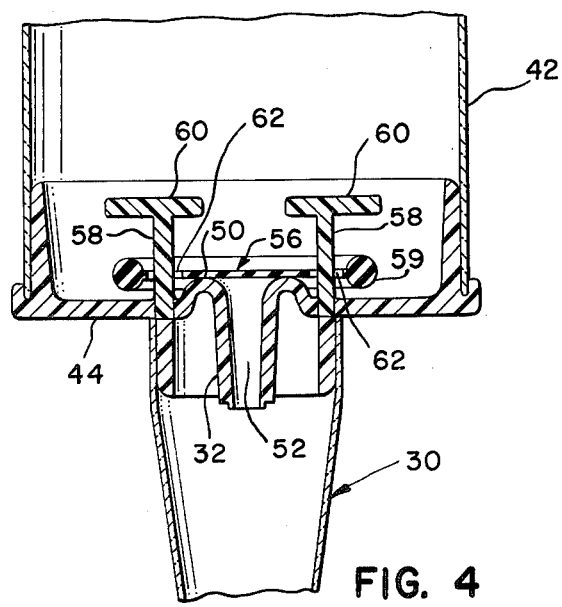
FIG. 4 is a partial side elevational view in cross section of a second embodiment of the valve means in the apparatus of FIG. 1.
Figure 7:
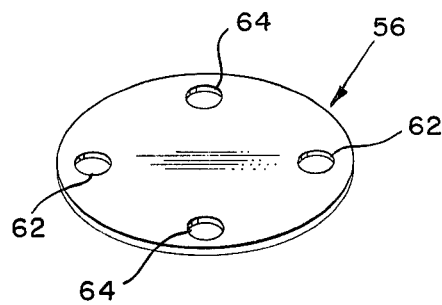
FIG. 7 is a perspective view of a modification of the float member used in the valve means of this invention.

Located at and associated with the outlet passage 52 is the improved valve means 14 which assures that air will not enter into the conduit 34 leading to the patient when the liquid level in the metering container reaches the outlet passage. Valve means 14 comprises a float member or disc 56 loosely retained by at least two generally upstanding posts 58 having their uppermost portions joined with disc-retaining bars or caps 60. Disc 56 is a thin sheet like member with a degree of flexibility sufficient for it to provide sealing of the outlet passage 52. It can be made of rubber, silicone rubber or any reasonably resilient plastic having the capability for floating on liquids. It can be a simple flat disc such as that shown in FIG. 7 or it can have the configuration shown in FIGS. 2 – 6 where the thin disc has a thickened rim 59 which assists in rigidifying the periphery of the disc. The rigidifying rim 59 can have other shapes such as a thickened portion extending from only one surface of the disc. This rim 59 also prevents large areas of the disc from sticking against the disc-retaining bars or stops 60 as liquid drops below the level of these stops. Disc-retaining stops 60 can be a single bar interconnecting the two (or more) posts 58 as in FIGS. 2 – 4 and 6, or stops 60 can be individual stops as in FIG. 4.

Figure 5:
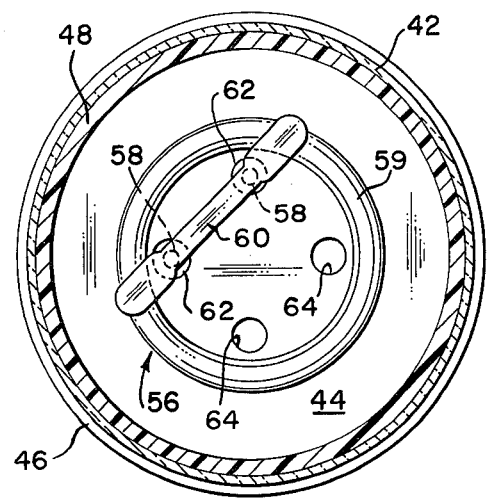
FIG. 5 is a top plan view of a third embodiment of the valve means.
Figure 6:
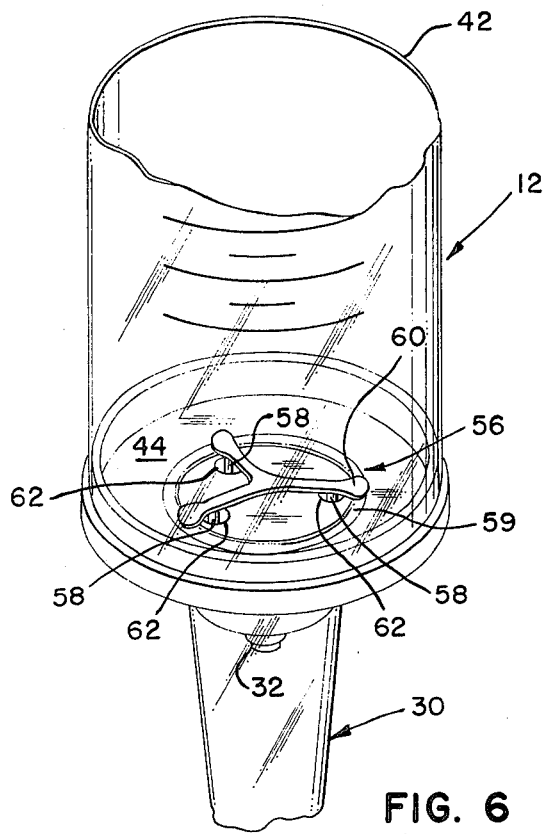
FIG. 6 is a fragmentary perspective view of a fourth embodiment of the valve means in the apparatus of FIG. 1.

The number of posts for guiding the disc 56 is not too critical, i.e., three or more posts can be used, although two posts are preferred and these two can be spaced at different distances around the valve seat 50. For example the two posts 58 are quite close to each other as shown in FIG. 5 or they can be more or less equally spaced from each other as in FIGS. 2 – 4 and 6.

Disc 56 is maintained in position over outlet passage 52 and yet remains unattached by means of the guiding posts 58 which extend through apertures 62 in disc 56. In order to assure that the disc 56 does not get hung up on the posts 58 should the disc become canted, the relationship of the size of the apertures 62 to the size of the posts 58 becomes a critical and important factor. To attain reliability in function of the valve, it has been found that the width of the aperture 62 should be at least twice the width of the post 58. With generally circular posts, the shape of the aperture can also be circular or some other configuration as for example an ovate shape. With ovate apertures, the width of the minor axis need not be at least twice that of the post width but the width of the major axis should conform to at least twice the width of the post with the major axis coinciding with the direction between the posts. For best results, the posts should be positioned slightly inwardly from the center of the apertures although valves in which the posts are exactly centered within the apertures of the disc or slightly outward from the center are quite satisfactory.

In the operation of the apparatus, with clamp 38 closed and clamp 22 open, solution from supply container 20 is allowed to flow into metering container 12 until somewhat more than the desired volume of solution has entered the metering container. Clamp 22 is then closed. The disc 56 at this point will generally be resting against the valve seat 50 by virtue of the greater pressure of the solution overlying the disc. The drip chamber 30 is squeezed to force air through outlet passage 52 which unseats disc 56 and allows it to float to the height of the retaining stop 60. When the drip chamber is partially filled, clamp 38 is opened to purge conduit 34 and needle 36 of air and solution allowed to flow from the needle until the desired level is reached in the metering container. Clamp 38 is then closed and a venipuncture performed for administering the preset volume of solution to the patient at a rate controlled by adjusting clamp 38. The rate of administration can be determined either by counting the drops per unit time passing from drip tube 32 or some other means for counting rate of flow which is associated with the conduit 34 can be used.

When the level of administered solution reaches the top of valve seat 50, the unapertured central portion of disc 56 automatically is in position over the valve seat and makes sealing contact with the valve seat to stop flow of solution and prevent air from passing beyond this point.

With the administration of certain kinds of solutions or fluids, as for example blood, foaming sometimes occurs and air in the foam can become trapped under the disc, rendering it inoperative. Usually this trapped air will pass upward through the apertures 62 into which posts 58 extend. However, better results are achieved if one or more air venting holes 64 are provided in the periphery of the disc 56 to help vent air bubbles and prevent air from passing down conduit 34 into the patient.

If an additional prescribed volume of solution is to be administered, the operation is repeated as heretofore described. In the step where a resiliently deformable member such as the drip chamber 30 or a squeeze bulb is sharply pressed to unseat the disc 56 from the valve seat 50, the posts 58 must be sufficiently long in order that the disc can rise a distance great enough to prevent its being sucked back or rebounding onto the valve seat when the pressure on the drip chamber or squeeze bulb is released. There is no hard and fast rule regarding minimum post length, however, since the unseating and rebounding actions depend not only on the size of the disc, but also on the size of the outlet passage 52, as well as on the amount of external pressure exerted on the deformable member and the rate at which this pressure is released. For most situations, however, a post length of about one-fourth of an inch or more between the top of the valve seat and the post stops should be quite adequate.

Metering device 12 when incorporated as a part of the administration assembly 10, need not be used solely for the administration of a smaller prescribed volume of solution as heretofore described. After filling the metering container 12 with enough solution to float the disc 56 and purging the set of air below the drip chamber 30, airway 26 may be closed by capping or other suitable means whereupon solution is then administered directly from supply container 20 (clamp 22 being released) to the patient. The valve 14 will of course close when all the solution from container 20 has been delivered.

The valve means 14 of this invention thus offers great improvement and reliability in assuring closure of an outlet passage in liquid administration containers when a liquid supply becomes exhausted and prevent air from passing beyond the outlet passage. The sealing disc, unlike those versions in which the disc is enclosed by a cage structure, remains unconfined so that air entrapment under and around the disc is avoided. In addition, the arrangement of the disc with the disc-positioning and retaining posts, in contrast to hinged disc valves, prevents canting when the disc must be in a position to seal the outlet passage.

The above-described embodiments are exemplary only and it will be understood that other modifications in form or detail can be made without departing from the scope of the invention.

What is claimed is:

1. Apparatus for dispensing a parenteral solution and for reliably controlling the cut off of fluid discharge, comprising
a. a metering container having a liquid inlet for communication with a source of liquid, a liquid outlet contained in a lower wall of the container, an air passage means for permitting air to enter the container when liquid is discharged from the container and for forming a liquid/air interface which moves toward the liquid outlet as liquid is discharged from the container and a resilient deformable means communicating with the liquid outlet for forcing fluid into the container through the liquid outlet upon manual compression;
b. valve means for normally closing off the liquid outlet whenever the liquid/air interface is above a predetermined minimum level and for initially opening the liquid outlet in response to reverse flow of fluid through the liquid outlet upon manual compression of said resilient deformable means and for permitting liquid to continue to flow out of the container only so long as the air/liquid interface is above the predetermined minimum level, said valve means including a floating valve disc having
   1. an unapertured central portion formed of sheet like material sufficiently thin and flexible to seal the liquid outlet of the container when in contact therewith and a peripheral portion containing at least a pair of apertures, and
   2. a rigidifying rim attached to the entire periphery of said central portion and extending upwardly above the upper surface of said central portion, said floatable valve disc being movable between a first position in which said central portion closes off the liquid outlet and a second position in which said floatable valve disc is spaced vertically above the container outlet by a distance which is significantly less than the vertical extent of the container but is sufficient to permit fluid to flow out of the container, said disc being buoyantly biased toward said second position whenever the liquid/air interface is above said second position and being carried toward said first position as the liquid/air interface descends from said second position to said first position; and
c. guiding and retaining means for guiding said disc between said first and second positions and retaining said disc in said second position against the bouyant forces on said disc whenever the liquid/air interface is above said second position and for reliably releasing said disc from said second position whenever the liquid/air interface descends below said second position, said guiding and retaining means including
   1. a pair of posts connected with the lower wall of the container adjacent the fluid outlet and extending upwardly through said apertures in said disc, said posts having a cross-sectional extent no greater than ½ the size of said apertures, and
   2. stop means mounted on said posts at a position to retain said disc against buoyant forces when said disc is in said second position, said stop means including a stop bar shaped to extend laterally by a distance which is significantly less than the lateral extent of said disc thereby to engage only a small portion of the circumference of said rigidifying rim of said disc when said disc is in said second position and thereby to prevent engagement between said stop bar and said central portion of said disc.

2. The apparatus of claim 1 wherein said disc includes a third aperture contained within said peripheral portion of said floating valve disc and said guiding and retaining means includes a third post connected with the lower wall of said container adjacent the fluid outlet and extending upwardly through said third aperture, said third post having a cross-sectional extent no greater than ½ the size of said apertures, said posts being spaced generally equidistant from each other.

3. The apparatus of claim 1 wherein the said stop bar is connected to the tops of and spans said posts.

4. The apparatus of claim 1 wherein said stop means includes an individual stop bar on the upper ends of each of said posts.

5. The apparatus of claim 1 wherein said disc is of uniform thickness.

6. The apparatus of claim 1 wherein said disc further includes at least one air-venting hole near the periphery of said disc and spaced between the pair of apertures.

7. The apparatus of claim 1 wherein said lower wall further includes a valve seat surrounding the outlet passage, said seat includes an annular bead projecting upwardly from said lower wall.

8. The apparatus of claim 1 wherein said lower wall includes a downwardly projecting tubular member and wherein said resilient deformable means includes a drip chamber connected at its upper end to said lower wall of said container, the upper portion of the drip chamber being spaced from and surrounding said tubular member.

* * * * *